US00PP35489P2

(12) United States Plant Patent
Fox

(10) Patent No.: US PP35,489 P2
(45) Date of Patent: Nov. 21, 2023

(54) ***KUNZEA* PLANT NAMED 'LFKULI19'**

(50) Latin Name: *Kunzea ericoides*
Varietal Denomination: LFKULI19

(71) Applicant: Ian Fox, Waipu (NZ)

(72) Inventor: Ian Fox, Waipu (NZ)

( * ) Notice: Subject to any disclaimer, the term of this patent is extended or adjusted under 35 U.S.C. 154(b) by 0 days.

(21) Appl. No.: 18/186,164

(22) Filed: Mar. 18, 2023

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of *Kunzea ericoides* named 'LFKULI19' is disclosed and is distinguishable by its weeping plant habit and dense stems and foliage which is very fine and soft to the touch. The leaves of 'LFKULI19' is aromatic and spicy. 'LFKULI19' is heat and drought tolerant and is hardy to USDA Zone 8. 'LFKULI19' rarely produces flowers.

1 Drawing Sheet

Genus and species: *Kunzea ericoides*.
Variety denomination: 'LFKULI19'.

BACKGROUND

The present disclosure relates to a new and distinct cultivar of *Kunzea ericoides*, commonly known as Kanuka and a native plant of New Zealand. In its native form, *Kunzea ericoides* grows as a medium to large sized tree with coarse foliage.

'LFKULI19' was discovered in 2018 by the inventor as a naturally occurring branch sport (a single shoot) with very fine foliage which was growing on a plant of *Kunzea ericoides* 'Little Fox' (unpatented). The sport parent 'Little Fox' was growing in a cultivated area in Waipu, New Zealand. The inventor excised and asexually propagated the discovered sport using the method of stem cuttings. The inventor has confirmed that 'LFKULI19' is stable and reproduces true to type in successive generations of asexual reproduction.

SUMMARY

The following traits have been repeatedly observed and represent the distinguishing characteristics of 'LFKULI19'. 'LFKULI19' has not been tested under all possible conditions and phenotypic differences may be observed with variations in environmental, climatic, and cultural conditions, without however, any variance in genotype.

1. 'LFKULI19' exhibits a dense slightly mounding weeping plant habit.
2. The foliage of 'LFKULI19' is very fine and soft to the touch.
3. The foliage of 'LFKULI19' is aromatic and spicy.
4. Plants achieve a height and spread of 15 cm by 60 cm after three years growth from planting a rooted cutting.
5. 'LFKULI19' rarely produces flowers.

6. 'LFKULI19' is heat and drought tolerant and is hardy to USDA Zone 8.

DESCRIPTION OF THE PHOTOGRAPH

The accompanying color photograph illustrates a three year old plant of 'LFKULI19' which has been growing out of doors in a 5-gallon container in Santa Barbara, Calif. The plant has been grown without any pruning or chemical treatment.

BOTANICAL DESCRIPTION OF THE NEW VARIETY

The following is a detailed botanical description of the new variety 'LFKULI19'. Data was collected from three year old plants which had been grown in five gallon containers out of doors in Santa Barbara, Calif. The color determinations are in accordance with the fifth edition (2007) of The Royal Horticultural Society Colour Chart of The Royal Horticultural Society, London, England, except where general color terms of ordinary dictionary significance are used. The plant has been grown without pruning or the use of growth-regulating chemicals.

Classification:
*Family.*—Myrtaceae.
*Genus.*—*Kunzea.*
*Species.*—*ericoides.*
*Common name.*—Kanuka.

Parentage: Naturally occurring branch shoot mutation found on parent plant *Kunzea ericoides* 'Little Fox'.

Plant:
*Form, habit.*—Mounding and weeping.
*Vigor.*—Vigorous with prolific basal branching.
*Propagation method.*—Softwood stem cuttings.
*Roots.*—Fine and fibrous, color 200B.
*Time to develop roots.*—4-5 weeks are required at air and soil temperate around 20° C. for a newly planted cutting to become established on its own roots.

*Crop time* (*from planting a rooted cutting*).—For a 1-gallon container, 1 year. For a 3-gallon container, 18 months to 2 years. For a 5-gallon container, 3 years.

*Uses*.—Planting in containers for outdoor standing, planting in garden borders or in the landscape in USDA Hardiness Zone 8 regions and warmer.

*Type*.—Perennial in USDA Zone 8 and warmer.

*Dimensions*.—15 cm in height measured from soil level, 120 cm in diameter at widest point. The tips of the weeping foliage lie between 8 cm and 10 cm below the soil level in the container.

*Cultural requirements*.—Grow in full sun or part shade with moderate water and well-draining soil.

*Hardiness*.—USDA Zone 8.

*Growth habit*.—Basal stems initially ascending, becoming pendulous.

*Heat and drought tolerance*.—High tolerance.

Stems, branches:

*Description*.—Short lignified base stem corresponding to the point of pinching or stopping the original transplanted rooted cutting. Primary branches form at the apex of the stem; secondary branches emerge alternately at every node of the primary branches. Except for dimensions, the primary branches and secondary branches exhibit identical characteristics.

*Stem*.—Shape: Terete. Dimensions: 3 cm in length, 2.5 cm in diameter. Surface: Lignified, rough. Color: 199B.

*Branches*.—Number: Approximately 15-20 primary branches and approximately 25-30 lateral branches per primary branch. Dimensions: Primary branches: 45 cm-55 cm in length and 1.5 mm-2.0 mm in diameter. Lateral branches: Oldest branches, 20 cm in length and 2 mm in diameter. Newer branches towards apex of primary branches, 6 cm in length and 1 mm in diameter. Internode distance between lateral branches: 5 cm-6 cm. Branch stem color: Ranges between 178A and 178B towards base, and 145C towards apex. Branch stem shape: Cylindrical. Branch stem texture: Glabrous. Branch stem strength: Firm and wiry.

Leaves:

*Type, arrangement*.—Simple, alternate.

*Attachment*.—Sessile.

*Quantity*.—Approximately 80 leaves per primary branch, basal stem, 50 leaves per lateral branch.

*Internode distance*.—1 mm-4 mm.

*Shape*.—Very narrowly lanceolate, almost linear.

*Dimensions*.—12 mm in length, 1.5 mm-2.0 mm in width.

*Texture, surface*.—Soft, glabrous, semi-glossy (both surfaces).

*Venation* (*both surfaces*).—Absent.

*Color* (*both surfaces*).—Older, lower leaves within the foliage canopy: 137B. New growth in shade (under the canopy): 139C. New growth exposed to full sun: 160A.

*Anthocyanin*.—Present on margins and adaxial surfaces of leaves exposed to full sun, anthocyanin color 185C.

*Margins*.—Smooth, entire, glabrous.

*Apex*.—Acute.

*Base*.—Acute.

*Fragrance*.—Aromatic, spicy, more evident when crushed.

Inflorescence:

*Incidence*.—The inventor in New Zealand has not observed any flowers on his plants from 2018 to date. Flowers have been observed once only in California, in July 2022, on a three years old plant. The flowers are very small and fall away completely after approximately 7 days.

*Number*.—5.

*Type*.—Capitulum.

*Bracts*.—5 leaf-like bracts subtend the hypanthium.

*Bract description*.—Narrowly lanceolate, 6 mm in length, 1 mm in width, color (both surfaces) 144A.

*Hypanthium*.—Obconical, 2 mm in height, 3 mm in diameter.

*Hypanthium color*.—178B (adaxial surface), 144A (abaxial surface).

*Petals*.—5 in number, free, rotate.

*Petal description*.—Obovate, 2.5 mm in length, 2 mm in width, apex rounded, base truncate, glabrous, color NN155D.

Reproductive organs:

*Stamens*.—18-20 in number, arranged around the perimeter of the hypanthium.

*Filaments*.—Fine, 3 mm in length, 0.5 mm in diameter at base, tapering to less than 0.5 mm at attachment to anthers, color NN155D.

*Anthers*.—Tiny, ellipsoid, 0.5 mm in length, 0.25 mm in diameter, color 12D.

*Pollen*.—None observed.

Seed: None observed.

Disease and pest resistance or susceptibility: None observed.

COMPARISON WITH PARENT

Whereas the parent plant, the cultivar *K. ericoides* 'Little Fox' grows as a large mounding shrub to 1.2 m high×1.5 m wide, with medium coarse foliage, 'LFKULI19' grows as a lightly mounding, ground cover shrub with very fine and soft weeping foliage.

COMPARISONS WITH KNOWN VARIETIES

The Applicant respectfully submits that the parent plant is the only known similar variety.

I claim:

1. A new and distinct cultivar of *Kunzea* plant named 'LFKULI19' as described and illustrated herein.

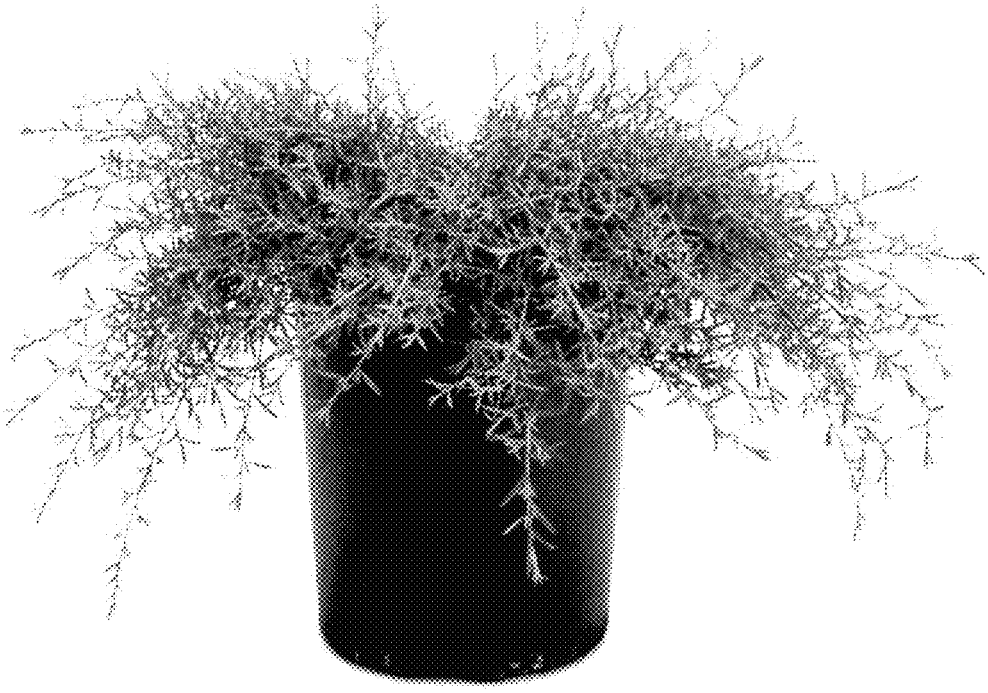

* * * * *